(12) United States Patent
Wulfert et al.

(10) Patent No.: US 8,846,652 B2
(45) Date of Patent: Sep. 30, 2014

(54) THERAPEUTIC USES OF STEROIDAL COMPOUNDS

(75) Inventors: Ernst Wulfert, Brussels (BE); James Robert Murray, Bristol (GB); David Wynick, Bristol (GB)

(73) Assignee: Hunter-Fleming Limited, Bristol (GB)

( * ) Notice: Subject to any disclaimer, the term of this patent is extended or adjusted under 35 U.S.C. 154(b) by 1301 days.

(21) Appl. No.: 12/094,079

(22) PCT Filed: Nov. 17, 2006

(86) PCT No.: PCT/GB2006/004305
§ 371 (c)(1),
(2), (4) Date: Oct. 28, 2008

(87) PCT Pub. No.: WO2007/057691
PCT Pub. Date: May 24, 2007

(65) Prior Publication Data
US 2009/0227551 A1   Sep. 10, 2009

(30) Foreign Application Priority Data
Nov. 18, 2005 (GB) .................................. 0523550.2

(51) Int. Cl.
| | | |
|---|---|---|
| A01N 43/00 | (2006.01) |
| A61K 31/33 | (2006.01) |
| A61K 31/56 | (2006.01) |
| A61K 31/568 | (2006.01) |
| A61K 31/573 | (2006.01) |

(52) U.S. Cl.
CPC ............. *A61K 31/568* (2013.01); *A61K 31/573* (2013.01)
USPC .......................................... 514/183; 514/179

(58) Field of Classification Search
CPC ........................... A61K 31/568; A61K 31/573
USPC ................................................. 514/183, 179
See application file for complete search history.

(56) References Cited

U.S. PATENT DOCUMENTS

| | | | | |
|---|---|---|---|---|
| 5,565,444 A | * | 10/1996 | Mizushima et al. ........... | 514/178 |
| 2009/0215731 A1 | * | 8/2009 | Birrell ........................... | 514/170 |

FOREIGN PATENT DOCUMENTS

| | | |
|---|---|---|
| EP | 0698612 | 2/1996 |
| JP | 6172387 | 6/1994 |
| JP | 9151197 | 6/1997 |
| JP | 00169374 | 6/2000 |
| WO | WO92/12997 | 8/1992 |
| WO | WO92/15015 | 9/1992 |
| WO | WO92/15681 | 9/1992 |
| WO | WO92/20709 | 11/1992 |
| WO | WO98/03059 | 1/1998 |
| WO | WO00/76522 | 12/2000 |
| WO | WO02/072084 | 9/2002 |
| WO | WO02/096934 | 12/2002 |
| WO | WO2005/080427 | 9/2005 |
| WO | WO2005/105104 | 11/2005 |
| WO | WO 2008/065408 | 6/2008 |

OTHER PUBLICATIONS

Joshi et. al. (Expert Opinion on Drug Discovery (2006) 1:341-352).*
Blakeman, KH et al. "Mice over-expressing galanin have elevated heat nociceptive threshold"; *NeuroReport* (2001) 12(2);423-425.
Counts, SE et al. "Galanin in Alzheimer Disease"; *Molecular Interventions* (2003) 3(3):137-156.
Ding, X et al. "Galanin attenuates β-amyloid (Aβ) toxicity in rat cholinergic basal forebrain neurons"; *Neurobiology of Disease* (2006) 21:413-420.
Eliott-Hunt, CR et al. "Galanin acts as a neuroprotective factor to the hippocampus"; *PNAS* (2004) 101(14)5105-5110.
Friesen, H et al. "Galanin—An Estrogen-regulated Pituitary Hormone"; *J. Endocrinol. Invest.* (1989) 12(5):25-33 (Abstract).
Hokfelt, T et al. "Increase of galanin-like immunoreactivity in at dorsal root ganglion cells after peripheral axotomy"; *Neuroscience Letters* (1987) 83:217-220.
Hokfelt, T et al. "Messenger plasticity in primary sensory neurons following axotomy and its functional implications"; *TINS* (1994) 17(1):21-30.
Holmes, FE et al "Targeted disruption of the galanin gene reduces the number of sensory neurons and their regenerative capacity"; *PNAS* (2000) 97(21):11563-11568.
Holmes, FE et al. "Transgenic overexpression of galanin in the dorsal root ganglia modulates pain-related behavior"; *PNAS* (2003) 100(10):6180-6185.
Hua, Z et al. "the Synthesis and Preliminary Biological Evaluation of a Novel Steroid with neurotrophic Activity: NGA0187"; *J. Org. Chem.* (2005) 70:9849-9856.
Hygge-Blakeman, K. et al. "Galanin over-expression decreases the development of neuropathic pain-like behaviors in mice after partial sciatic nerve injury"; *Brain Research* (2004) 1025:152-158.
Mahoney, S-A et al. "The Second Galanin Receptor GalR2 Plays a Key Role in Neurite Outgrowth from Adult Sensory Neurons"; *J. Neurosci.* (2003) 23(2):416-421.

(Continued)

*Primary Examiner* — Marcos Sznaidman
(74) *Attorney, Agent, or Firm* — Lathrop & Gage LLP

(57) ABSTRACT

A steroid derivative compound of formula (I) in which: one of $R^1$ and $R^2$ is hydroxy and the other is hydrogen; or $R^1$ and $R^2$ together represent oxo; $R^3$ is hydrogen or hydroxy; and the dotted lines represent single or double carbon-carbon bonds; and pharmaceutically acceptable salts and esters thereof are useful for the prevention or treatment of pain, for improving nerve regeneration after nerve injury or damage or disease, for the prevention or treatment of brain injury, damage or disease and for neuroprotection. Particularly useful compounds are 11-hydroxy-Δ4-androstene-3,17-dione and 11-oxo-Δ4-androstene-3,17-dione or their derivatives.

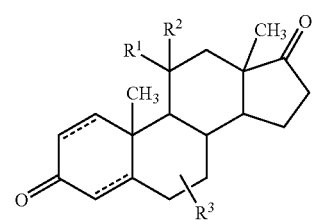

(I)

6 Claims, 1 Drawing Sheet

(56) References Cited

OTHER PUBLICATIONS

Mazarati, AM et al. "Modulation of Hippocampal Excita bility and Seizures by Galanin"; *J. Neurosci.* (2000) 20(16):6276-6281.

Pirondi, S et al. "The galanin-R2 agonist AR-M1896 reduces glutamate toxicity in primary neural hippocampal cells"; *J. Neurochem.* (2005) 95:821-833.

Tatemoto, K et al. "Galanin—a novel biologically active peptide from porcine intestine"; *FEBS* (1982) 164(1):124-128.

Wu, W-P et al. "Systemic galnon, a low-molecular weight galanin receptor agonist, reduces heat hyperalgesia in rats with nerve injury"; *Euro. J. Pharmacol.* (2003) 482:133-137.

Erichsen et al., 2005, Pain, 116(3):347 (Abstract only).
Rode et al., 2005, Eur. J. Pharmacol., 516(2):131 (Abstract only).
Rowbotham et al., 2005, J. Rheumatol. Supp., 75:38 (Abstract only).
Rho et al., 2002, May Clin. Proc., 77:174 (Abstract only).
Oh et al., 2003, American Family Physician, 67(5):979-986.
Burstein and Winer, 2007, Journal of Clinical Oncology, 25:3797-3799.
Campbell and Meyer, 2006, Neuron, 52:77-92.
Costigan et al., 2009, Annu. Rev. Neurosci., 32:1-32.
Portenoy and Lesage, 1999, Lancet, 353:1695-1700.
Sehdev et al., 2009, Current Oncology 16 (Supplement 2): S14-S23.
Thorne, C., 2007, Current Oncology, 14 (Supplement 1): S11-S19.

* cited by examiner

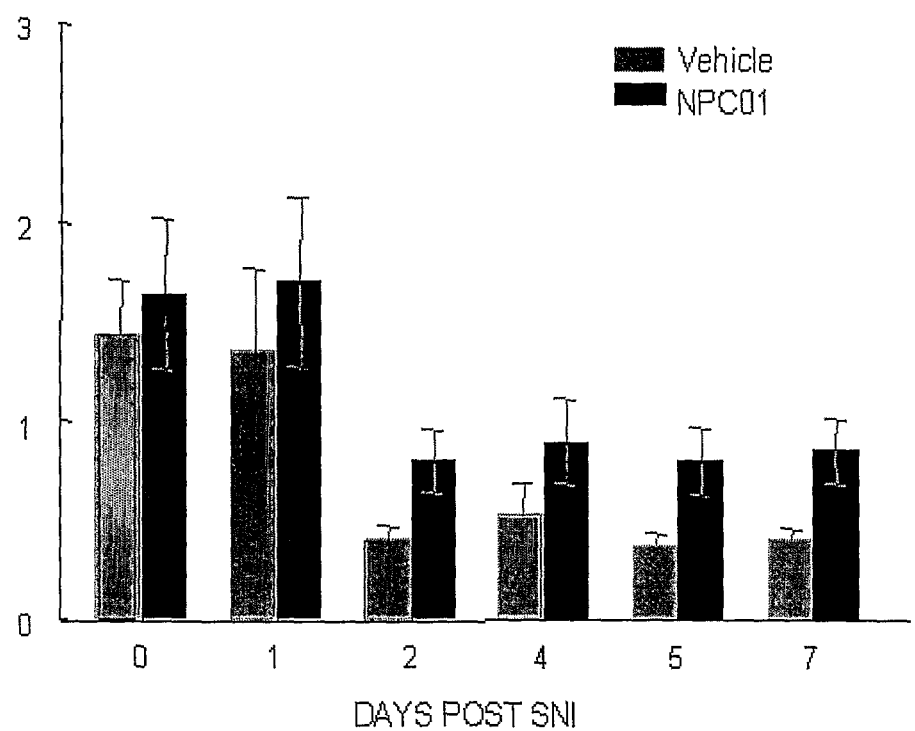

THERAPEUTIC USES OF STEROIDAL COMPOUNDS

CROSS-REFERENCE TO RELATED APPLICATIONS

This application is the U.S. National Stage of International Application No. PCT/GB2006/004305, filed Nov. 17, 2006 and published in English on May 24, 2007 as WO 2007/057691 A2, which claims the benefit of GB Application 0523550.2, filed Nov. 18, 2005, both of which are hereby incorporated by reference in their entirety to the extent not inconsistent with the disclosure herein.

This invention relates to the therapeutic uses of steroid derivatives in the treatment or prevention of pain, especially, but not exclusively, neuropathic or inflammatory pain, nerve injury and neuroprotection. In particular, the invention relates to the use of certain hydroxysteroid derivatives, such as 11-hydroxy-$\Delta$4-androstene-3,17-dione or 11-oxo-$\Delta$4-androstene-3,17-dione. More specifically, the invention relates to the use of these compounds, especially 11$\beta$-hydroxy-$\Delta$4-androstene-3,17-dione, in the treatment or prevention of pain and/or promotion of nerve regeneration or repair and/or neuroprotection.

Injury to a peripheral nerve induces changes within the cell bodies of sensory neurons located in the dorsal root ganglion (DRG) that promote survival and axonal regeneration. Under favourable conditions, for instance following a crush injury, most nerve fibres successfully regenerate. However, in many clinically relevant circumstances, traumatic or disease-induced nerve injury has a poor outcome with only a limited return of function and often with considerable delay. In such cases, neuropathic or chronic pain states may develop.

Pain is normally associated with injury or damage and results in guarding and immobilisation of the affected area. Nociception (the neuronal signalling underlying the sensation of pain) therefore, results in protection and the promotion of rapid healing, albeit triggering an unpleasant sensory and emotional experience. In many pathological situations, nociceptive inputs can result in functional changes that are actively detrimental to the organism.

Chronic inflammation or nerve injury results in the alteration of many of the properties of primary afferent neurons and their central connections in the spinal cord, leading to allodynia (the perception of pain from a normally innocuous stimulus), hyperalgesia (an exaggerated response to any given pain stimulus) and an expansion of the receptive field (i.e. the area that is "painful" when a stimulus is applied). The majority of chronic pain conditions arise as a result of damage to either central or peripheral nervous tissue.

Neuropathic pain can be defined as pain deriving from damage to, or inflammation of, the central or peripheral nervous systems. Examples of pain syndromes and causes of pain of this class include painful diabetic sensory neuropathy, alcoholic neuropathy, trigeminal neuralgia, cancer-related pain due to tumour invasion of a nerve, post-herpetic neuralgia, temporomandibular disorder, myofascial pain, back pain (sciatica), peripheral nerve or spinal cord trauma or transection (including surgery), limb amputation and stump pain, arteriovenous malformations, Vitamin B12 deficiency, pain caused by the side-effects of anti-cancer and anti-AIDS therapies, post-stroke pain, complex regional pain syndrome, fibromyalgia-associated neuropathic pain, reflex sympathetic dystrophy, phantom limb syndrome, multiple sclerosis-associated pain, HIV-associated neuropathic pain, carpal tunnel-associated neuropathic pain, pain associated with inflammation or infection of a tooth (toothache), or visceral pain.

Similarly, pain ("inflammatory pain") may also be induced by inflammatory conditions such as connective tissue diseases which include, without limitation, rheumatoid arthritis, Wallenberg's syndrome, systemic lupus erythematosus, multiple sclerosis and polyarteritis nodosa. In addition, inflammatory pain may be caused by various chemical burns and various local and systemic infections.

Neuropathic pain may occur in all body regions. Burn injury also often leads to neuropathic hyperalgesia in the affected body area. In humans, neuropathic pains tend to be chronic. There is general agreement amongst clinicians that neuropathic pain is usually resistant, non-responsive, or only partially responsive to treatment with opioid analgesics. Consequently, alternate therapies for the management of neuropathic pain are widely sought. These include the use of anti-depressants and anti-epileptics, and most recently the drugs gabapentin and pregabalin. Both classes of drugs are effective in only 25-35% of cases. Further, the beneficial effects of these drugs are short lived, rarely persist after a few weeks or months and are often at the expense of severe side-effects. Side effects of these classes of drugs include sedation, confusion, abdominal pain, diarrhoea, vomiting, renal toxicity and liver toxicity. Similarly, current therapies for inflammatory pain include drugs in the classes of non-steroidal anti-inflammatories and cyclo-oxygenase-II (cox-2) inhibitors. Both these classes of drugs have major side-effects including gastrointestinal upset, nausea and vomiting, gastrointestinal bleeding and gastritis. Cox-2 inhibitors have also recently been implicated in cardiovascular disorders, including heart attacks and stroke.

In recent years, a number of compounds have been identified that modulate neuropathic and/or inflammatory pain behaviour. For example:

WO-A-03/007936 relates to the use of carbamate compounds for the prevention and treatment of neuropathic pain;

WO-A-03/011289 and US-A-2003/0087965 relate to the use of 3-heterocyclo and 3-cycloalkyloxy-3-phenylpropanamines in the treatment of chronic pain, including neuropathic pain;

WO-A-03/032910 relates to the use of carbinols in the treatment of neuropathic pain; and EP-A-1243262 relates to the use of a known class of chemical compounds in the treatment of inflammatory pain, for example, rheumatoid arthritis pain. The compounds are also said to show antinociceptive effects.

The patho-physiological mechanisms that underlie neuropathic pain and its relationship to disordered peripheral nerve regeneration are poorly understood and remain important clinical and scientific issues. Many research groups have attempted to further elucidate the mechanisms that underlie the adaptive response of the peripheral nervous system to injury, by studying factors and/or receptors whose levels and expression patterns are known to change in primary sensory neurons after injury, for example, neurotrophins, the TGF$\beta$ superfamily, and various neuropeptides and their receptors. One such neuropeptide is galanin.

Galanin is a twenty-nine amino-acid neuropeptide and was originally isolated from porcine intestine in 1983 [K. Tatemoto, A. Rokaeus, H. Jornvall, T. J. McDonald, and V. Mutt. Galanin—a novel biologically active peptide from porcine intestine. FEBS Lett. 164:124-128, (1983)]. It is expressed at low levels in <5% of intact (uninjured) adult DRG neurons, which are predominantly small diameter C-fibre nociceptors [T. Hokfelt, Hallin Z. Wiesenfeld, M. Villar, and T. Melander. Increase of galanin-like immunoreactivity in rat dorsal root ganglion cells after peripheral axotomy. Neurosci. Lett. 83:217-220, (1987)]. After nerve section (axotomy), galanin mRNA and peptide levels rise by up to 120-fold, and are abundantly expressed in 40-50% of all DRG (dorsal root ganglion) neurons [T. Hokfelt, Hallin Z. Wiesenfeld, M. Villar, and T. Melander. Increase of galanin-like immunoreactivity in rat dorsal root ganglion cells after peripheral axotomy. Neurosci. Lett. 83:217-220, (1987)]. The levels of the peptide remain elevated whilst the nerve is regenerating [T. Hokfelt, X. Zhang, and Hallin Z. Wiesenfeld. Messenger plasticity in primary sensory neurons following axotomy and its functional implications. Trends. Neurosci. 17:22-30, (1994)].

To study the role played by galanin in the adaptive response of the nervous system to injury further, various novel strains of transgenic mice in which galanin over-expression (Gal-OE) is targeted to the DRG, were generated [F. E. Holmes, A. Bacon, R. J. Pope, P. A. Vanderplank, N. C. Kerr, M. Sukumaran, V. Pachnis, and D. Wynick. Transgenic overexpression of galanin in the dorsal root ganglia modulates pain-related behaviour. Proceedings of the National Academy of Sciences of the United States of America 100 (10):6180-6185, (2003), and A. M. Mazarati, J. G. Hohmann, A. Bacon, H. Liu, R. Sankar, R. A. Steiner, D. Wynick, and C. G. Wasterlain. Modulation of hippocampal excitability and seizures by galanin. J. Neurosci. 20 (16):6276-6281, (2000), and K. H. Blakeman, K. Holmberg, J. X. Hao, X. J. Xu, U. Kahl, U. Lendahl, T. Bartfai, Z. Wiesenfeld-Hallin, and T. Hokfelt. Mice over-expressing galanin have elevated heat nociceptive threshold. Neuroreport 12 (2):423-425, (2001)]. Many of these over-expressing lines of mice have markedly increased latencies to both mechanical and thermal testing in the intact adult [F. E. Holmes, A. Bacon, R. J. Pope, P. A. Vanderplank, N. C. Kerr, M. Sukumaran, V. Pachnis, and D. Wynick. Transgenic overexpression of galanin in the dorsal root ganglia modulates pain-related behaviour. Proceedings of the National Academy of Sciences of the United States of America 100 (10):6180-6185, (2003) and K. H. Blakeman, K. Holmberg, J. X. Hao, X. J. Xu, U. Kahl, U. Lendahl, T. Bartfai, Z. Wiesenfeld-Hallin, and T. Hokfelt. Mice over-expressing galanin have elevated heat nociceptive threshold. Neuroreport 12 (2):423-425, (2001) and K. Hygge-Blakeman, P. Brumovsky, J. X. Hao, X. J. Xu, T. Hokfelt, J. N. Crawley, and Z. Wiesenfeld-Hallin. Galanin over-expression decreases the development of neuropathic pain-like behaviours in mice after partial sciatic nerve injury. Brain Research 1025 (1-2):152-158, (2004)]. They also show a marked reduction in mechanical allodynia (neuropathic pain behaviour) in a number of differing models of neuropathic pain [F. E. Holmes, A. Bacon, R. J. Pope, P. A. Vanderplank, N. C. Kerr, M. Sukumaran, V. Pachnis, and D. Wynick. Transgenic overexpression of galanin in the dorsal root ganglia modulates pain-related behaviour. Proceedings of the National Academy of Sciences of the United States of America 100 (10):6180-6185, (2003) and K. Hygge-Blakeman, P. Brumovsky, J. X. Hao, X. J. Xu, T. Hokfelt, J. N. Crawley, and Z. Wiesenfeld-Hallin. Galanin over-expression decreases the development of neuropathic pain-like behaviours in mice after partial sciatic nerve injury. Brain Research 1025 (1-2): 152-158, (2004)]. These data support the hypothesis that galanin plays an inhibitory role in pain processing in the intact animal and especially following nerve injury. These analyses, coupled with the use of a number of galanin pharmacological tools, have produced a very large body of data demonstrating that, after nerve injury, when endogenous levels of galanin are high, galanin plays an inhibitory role in pain transmission.

In addition to the pain modulating role played by galanin, it has been shown that galanin stimulates peripheral nerve regeneration and neurite outgrowth from cultured adult mouse DRG neurons. The rate of peripheral nerve regeneration following crush injury to the sciatic nerve was reduced by 35% in adult galanin knock-out animals and was associated with long-term sensorimotor functional deficits [F. E. Holmes, S. Mahoney, V. R. King, A. Bacon, N. C. H. Kerr, V. Pachnis, R. Curtis, J. V. Priestley, and D. Wynick. Targeted disruption of the galanin gene reduces the number of sensory neurons and their regenerative capacity. Proc Natl Acad Sci USA 97 (21):11563-11568, (2000)]. Furthermore, this compromised regenerative capacity in-vivo was reflected by in-vitro deficits in neuritogenesis, as determined by the ability of dissociated DRG cells to extend neurites in culture. The number of adult galanin knock-out cells producing neurites was reduced by a third compared to wild-type controls whilst mean neurite length was halved [F. E. Holmes, S. Mahoney, V. R. King, A. Bacon, N. C. H. Kerr, V. Pachnis, R. Curtis, J. V. Priestley, and D. Wynick. Targeted disruption of the galanin gene reduces the number of sensory neurons and their regenerative capacity. Proc Natl Acad Sci USA 97 (21): 11563-11568, (2000)]. To confirm that this reduction in neurite length was due to the lack of galanin in the adult, rather than developmental changes, galanin peptide was added to cultures from adult wild-type and galanin knockout animals. The addition of galanin peptide significantly enhanced neurite outgrowth from wild-type sensory neurons and fully rescued the observed deficits in galanin knockout cultures [S. A. Mahoney, R. Hosking, S. Farrant, F. E. Holmes, A. S. Jacoby, J. Shine, T. P. Iismaa, M. K. Scott, R. Schmidt, and D. Wynick. The second galanin receptor GalR2 plays a key role in neurite outgrowth from adult sensory neurons. J. Neurosci. 23 (2): 416-421, (2003)]. These results demonstrate that adult sensory neurons are dependent upon galanin for neurite extension and peripheral nerve regeneration.

Similar to the trophic and growth-promoting role played by galanin in peripheral sensory neurons, there is increasing data to show that galanin plays an analogous role in the central nervous system. Galanin acts as an endogenous neuroprotective factor to the hippocampus in a number of in-vivo and in-vitro models of injury, implying that galanin or a galanin agonist would have therapeutic uses in various forms of brain disease and brain injury [C. R. Elliott-Hunt, B. Marsh, A. Bacon, R. Pope, P. Vanderplank, and D. Wynick, "Galanin acts as a neuroprotective factor to the hippocampus", Proceedings of the National Academy of Sciences of the United States of America 101:5105-5110, (2004); and S. Pirondi, M. Fernandez, R. Schmidt, T. Hokfelt, L. Giardino, and L. Calza "The galanin-R2 agonist AR-M1896 reduces glutamate toxicity in primary neural hippocampal cells" Journal Of Neurochemistry 95 (3):821-833, (2005)], including Alzheimer's Disease [PCT/GB2005/000188; and S. E. Counts, S. E. Perez, S. D. Ginsberg, S. De Lacalle, and E. J. Mufson "Galanin in Alzheimer disease" Molecular Interventions 3 (3): 137-156, (2003); and Xiling Ding, David MacTavish, Satyabrata Kar, and Jack H. Jhamandas, "Galanin attenuates beta-amyloid (A[beta]) toxicity in rat cholinergic basal forebrain neurons", Neurobiology of Disease In Press] and multiple sclerosis [PCT/GB2005/000188].

Kainate-induced hippocampal cell death was greater in regions of galanin knockout animals than in wild-type controls. Exposure to glutamate or staurosporine, induced significantly more neuronal cell death in galanin knockout organotypic and dispersed primary hippocampal cultures than in WT controls. Conversely, less cell death was observed in the hippocampus of galanin over-expressing transgenic animals after kainate injection and in organotypic cultures after exposure to staurosporine. Further, exogenous galanin reduced cell death when co-administered with glutamate or staurosporine in wildtype cultures [C. R. Elliott-Hunt, B. Marsh, A. Bacon, R. Pope, P. Vanderplank, and D. Wynick, "Galanin acts as a neuroprotective factor to the hippocampus" Proceedings of the National Academy of Sciences of the United States of America. 101:5105-5110, (2004)]. Galanin also reduced hippocampal damage in wild-type mice induced by A-beta peptide (the aetiological agent in AD), caused more damage in galanin knockout animals and less damage in galanin over-expressing animals [PCT/GB2005/000188]. Further, using the experimental allergic encephalitis (EAE) model of MS, galanin knock out animals developed more severe disease at an earlier time point than control animals, whilst galanin over-expressing animals were resistant to the development of any disease in the EAE model [PCT/GB2005/000188]. These data again demonstrate that galanin plays a neuroprotective role to the brain and spinal cord in many differing disease states.

WO92/12997 discloses the sequence of human galanin and its uses in pain.

WO92/20709 discloses a number of putative galanin antagonists. The antagonists which are described are all based on the first 12 amino acids of galanin followed by partial sequences of other peptides i.e. chimeric peptides, and may be useful as analgesics.

JP-A-6172387 discloses a synthetic peptide and derivatives for effectively inhibiting the insulin-secretion suppressing action of galanin which peptide is expected to be useful as a galanin-antagonistic substance for the prevention and treatment of Alzheimer's Disease.

WO92/15681 discloses a peptide having the amino acid sequence of human galanin and DNA clones encoding the peptide. It is suggested that galanin may play a role in pancreatic activity and claims methods of modulating pancreatic activity, or of stimulating the production of growth hormone, the methods involving the use of the disclosed peptides.

WO92/15015 discloses DNA encoding human galanin and methods for the identification of galanin antagonists.

EP-A-0918455 discloses that recovery from crush injury (indicative of the regenerative abilities of sensory axons in the sciatic nerve), neuron survival during development and long term potentiation (LTP) are reduced in mice lacking the galanin gene compared to wild-type mice. There is also disclosed a mouse, which has been engineered such that it lacks the galanin gene.

WO02/096934 discloses a series of galanin agonist compounds which may be used to treat convulsive seizures such as those which take place in epilepsy. These are complex organic compounds and one of these compounds, named "galnon" [Wu et al. (2003) Eur. J. Pharmacol. 482 133-137] equally activates and has agonistic activity to both GALR1 and GALR2 and has uses in treating pain.

Thus, the above data demonstrate that the administration in rodents of exogenous galanin or the transgenic up-regulation of endogenous galanin levels both markedly inhibit neuropathic pain behaviour and stimulate peripheral nerve regeneration and axonal outgrowth. Similarly, galanin plays a neuroprotective role to the brain and spinal cord in a range of disease models that include stroke, brain damage, AD or MS.

To date, the mechanisms that regulate galanin expression in the nervous system and particularly the adult DRG or spinal cord, and the responses to nerve injury are unknown. Similarly, no compounds or drugs have been identified that modulate galanin expression in the DRG or spinal cord, in contrast to galanin expression in the pituitary gland, which is stimulated by chronic oestrogen exposure [M. E. Vrontakis and H. G. Friesen. Galanin an estrogen regulated hormone of the anterior pituitary gland. Proceedings of the 4th Meeting of the European Neuroendocrine Association:25-33, (1989)].

None of the compounds discussed above are steroidal. The inventors have now surprisingly found that certain steroid derivatives are effective in reducing pain in the SNI (spared nerve injury) model.

Thus, the present invention, in one aspect, consists in the use of a compound of formula (I):

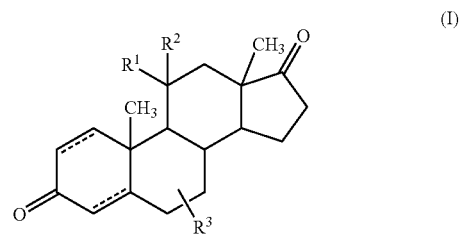

(in which:
one of $R^1$ and $R^2$ represents a hydroxy group and the other represents a hydrogen atom; or
$R^1$ and $R^2$ together represent an oxo group;
$R^3$ represents a hydrogen atom or a hydroxy group; and
the dotted lines represent single or double carbon-carbon bonds);
and pharmaceutically acceptable salts and esters thereof for the preparation of a medicament for the prevention of or the treatment of pain.

In the compounds of the present invention, where $R^1$ or $R^2$ represents a hydroxy group, this is preferably in the beta configuration.

Examples of such compounds are 11-hydroxy-Δ4-androstene-3,17-dione and 11-oxo-Δ4-androstene-3,17-dione. These are physiological substances that are synthesized from androstenedione (Δ4-androstene-3,17-dione) by an 11β hydroxylase that exists in the body in the adrenal cortex and by side-chain cleavage in position 17 of the glucocorticoid cortisol. A preferred compound is 11β-hydroxy-Δ4-androstene-3,17-dione (11β-OH-A).

The steroid derivative of formula (I) or a pharmaceutically acceptable salt or ester thereof may be given alone or in combination with other known treatments for pain such as gabapentin or pregabalin.

According to another aspect of the invention there is provided a method for preventing or treating a subject for pain comprising administering an effective amount of a steroid derivative of formula (I) or a pharmaceutically acceptable salt or ester thereof. Preferably, the compounds are 11-hydroxy-Δ4-androstene-3,17-dione and 11-oxo-Δ4-androstene-3,17-dione or their derivatives. In particular, the compound is most preferably 11β-hydroxy-Δ4-androstene-3,17-dione (11β-OH-A). The steroid derivative may be given alone or in combination with other known treatments for pain, such as gabapentin or pregabalin.

The pain may be neuropathic pain, preferably centrally mediated neuropathic pain. The pain may be chronic, allodynia (the perception of pain from a normally innocuous stimulus), hyperalgesia (an exaggerated response to any given pain stimulus) and an expansion of the receptive field (i.e. the area that is "painful" when a stimulus is applied), phantom pain or inflammatory pain.

In a further alternative, the pain may be one of painful diabetic peripheral neuropathy, post-herpetic neuralgia, trigeminal neuralgia, post-stroke pain, multiple sclerosis-associated pain, neuropathy-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathetic dystrophy, phantom limb syndrome or peripheral nerve or spinal cord trauma, entrapment neuropathy, nerve transection including surgery, Lissauer tract section, limb amputation and stump pain, neuroma/tumour compression, arteriovenous malformation, Vitamin B12 deficiency, diabetic neuropathy, alcoholic neuropathy, pain caused by the side effects of anti-cancer and anti-AIDS therapies, pain associated with inflammation or infection of a tooth (toothache), visceral pain, pain caused by chemical burns, pain caused by local or systemic infection, or pain caused by connective tissue disease. The connective tissue disease may be one of: rheumatoid arthritis, Wallenberg's syndrome, systemic lupus erythematosus, multiple sclerosis, or polyarteritis nodosa.

The pain may be associated with cancer, surgery, visceral damage, headache or trauma.

According to a further aspect of the present invention there is provided the use of a steroid derivative of formula (I) or a pharmaceutically acceptable salt or ester thereof for the preparation of a medicament for the prevention of or protection against brain damage, brain injury or brain disease, or an improvement in the condition of individuals who have suffered such brain damage, injury or disease. Preferably, the compounds are 11-hydroxy-Δ4-androstene-3,17-dione or 11-oxo-Δ4-androstene-3,17-dione or their derivatives. In particular, the compound is most preferably 11β-hydroxy-Δ4-androstene-3,17-dione. Other suitable derivatives are also contemplated for use in accordance with the invention.

According to another aspect of the invention there is provided a method for prevention of or protection against brain damage, injury or disease, or an improvement in the condition of individuals who have suffered such brain damage, injury or disease comprising administering an effective amount of a steroid derivative of formula (I) or a pharmaceutically acceptable salt or ester thereof. Preferably, the compounds are 11-hydroxy-Δ4-androstene-3,17-dione and 11-oxo-Δ4-androstene-3,17-dione or their derivatives. In particular, the compound is most preferably 11β-hydroxy-Δ4-androstene-3,17-dione.

The brain injury or brain damage may be caused by one of embolic, thrombotic or haemorrhagic stroke, direct or indirect trauma or surgery to the brain or spinal cord, ischaemic or embolic damage to the brain during cardiopulmonary bypass surgery or renal dialysis, reperfusion brain damage following myocardial infarction, brain disease, immunological damage, chemical damage or radiation damage. The immunological damage may be the result of bacterial or viral infection. The chemical damage may be the result of excess alcohol consumption or administration of chemotherapy agents for cancer treatment. The radiation damage may be the result of radiotherapy for cancer treatment.

The brain disease is preferably one of Alzheimer's Disease (AD), Parkinson's Disease (PD), Multiple Sclerosis (MS) or variant Creutzfeld Jacob Disease (CJD).

According to a still further aspect of the invention there is provided the use of a steroid derivative of formula (I) or a pharmaceutically acceptable salt or ester thereof for the preparation of a medicament for the promotion of nerve regeneration, nerve repair or neuroprotection. Preferably, the compounds are 11-hydroxy-Δ4-androstene-3,17-dione and 11-oxo-Δ4-androstene-3,17-dione or their derivatives. In particular, the compound is most preferably 11β-hydroxy-Δ4-androstene-3,17-dione.

Advantageously, these compounds may allow the promotion of nerve regeneration and/or repair, as the result of following, for example, nerve injury, disease or damage, including AD, PD and MS.

According to another aspect of the invention there is provided a method of promoting nerve regeneration, nerve repair or neuroprotection in a subject comprising administering to the subject an effective amount of a steroid derivative of formula (I) or a pharmaceutically acceptable salt or ester thereof. Preferably, the compound is selected from 11-hydroxy-Δ4-androstene-3,17-dione and 1-oxo-Δ4-androstene-3,17-dione or their derivatives.

The compounds of the present invention can be used to repair nerve damage injury or disease in any condition where there is nerve damage or nerve loss, such as due to ischaemia or hypoxia. Nerve damage or loss may be due to chronic neurodegenerative condition such as in Alzheimer's disease or Parkinson's disease. Similarly, the compounds of the present invention can be used to treat multiple sclerosis.

According to another aspect of the invention there is provided a pharmaceutical composition for use in the treatment or prevention of pain, the composition comprising an effective amount of at least one of an steroid derivative of formula (I) or a pharmaceutically acceptable salt or ester thereof. Preferably, the composition comprises 11-hydroxy-Δ4-androstene-3,17-dione or 11-oxo-Δ4-androstene-3,17-dione or their derivatives, and a suitable excipient. Most preferably, the composition comprises 11β-hydroxy-Δ4-androstene-3,17-dione.

According to a further aspect of the invention there is provided a pharmaceutical composition for use in the treatment or prevention of brain damage, brain injury or brain disease, or an improvement in the condition of individuals who have suffered such brain damage, injury or disease, the composition comprising an effective amount of a steroid derivative of formula (I) or a pharmaceutically acceptable salt or ester thereof. Preferably, the composition comprises at least one of 11-hydroxy-Δ4-androstene-3,17-dione or 11-oxo-Δ4-androstene-3,17-dione or their derivatives and a suitable excipient. Most preferably, the composition comprises 11β-hydroxy-Δ4-androstene-3,17-dione.

Conveniently, these compounds may prevent or reduce cell death.

The invention also provides a pharmaceutical composition for use in the promotion of nerve regeneration, or nerve repair, and neuroprotection, the composition comprising an effective amount of an steroid derivative of formula (I) or a pharmaceutically acceptable salt or ester thereof and a suitable excipient. Preferably the composition comprises at least one of 11-hydroxy-Δ4-androstene-3,17-dione or 11-oxo-Δ4-androstene-3,17-dione or their derivatives.

Pharmaceutical compositions of this invention may comprise one or more or a combination of the steroid derivatives of formula (I) and pharmaceutically acceptable salts or esters thereof, with any pharmaceutically acceptable carrier, adjuvant or vehicle.

Pharmaceutically acceptable carriers, adjuvants and vehicles that may be used in the pharmaceutical compositions of this invention include, for example, ion exchangers, alumina, aluminium stearate, lecithin, serum proteins such as human serum albumin, buffer substances such as phosphates, glycine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. One or more of the esters may be used as a prodrug.

Pharmaceutical compositions of this invention may be administered orally, parenterally, by injection, by needle-free device, by inhalation spray, topically, rectally, nasally, buccally, vaginally or via an implanted reservoir. Oral administration or administration by injection or needle-free device is preferred. The term "parenteral" as used herein includes subcutaneous, intracutaneous, intravenous, intramuscular, intra-articular, intrasynovial, intrasternal, intrathecal, intralesional and intracranial injection or infusion techniques.

Where the pharmaceutical composition is administered by injection or needle-free device, it may be in the form of a sterile injectable preparation or a form suitable for delivery by needle-free device, which may be an aqueous or oleaginous suspension. This suspension may be formulated according to techniques known in the art using suitable dispersing or wetting agents (such as, for example, Tween 80) and suspending agents. The sterile injectable preparation or form suitable for delivery by needle-free device may also be a solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

Pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, can also typically be added. For oral administration in a capsule form, useful diluents include lactose and dried corn starch. When aqueous suspensions are administered orally, the active ingredient is combined with emulsifying and suspending agents. If desired, sweetening and/or flavouring and/or colouring agents may be added.

Pharmaceutical compositions of this invention may also be administered in the form of suppositories for rectal administration. These compositions can be prepared by mixing a compound of this invention with a suitable non-irritating excipient which is solid at room temperature but liquid at rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene-polyoxypropylene compounds, emulsifying wax and water. Alternatively, the pharmaceutical composition can be formulated with a suitable lotion or cream containing the active compound suspended or dissolved in a carrier. Suitable carriers include, for example, mineral oil, sorbitan monostearate, polysorbate 60, cetyl esters wax, cetearyl alcohol, 2-octyldodecanol, benzyl alcohol and water. Pharmaceutical compositions of this invention may also be topically applied to the lower intestinal tract by rectal suppository formulation or in a suitable enema formulation. Topical-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

BRIEF DESCRIPTION OF DRAWING

The invention is further illustrated by reference to the following non-limiting Examples and drawings in FIG. 1 in which:

FIG. 1 is a histogram illustrating the results of experiments on the effect of daily oral administration of 11β-hydroxy-Δ4-androstene-3,17-dione on mechanical nociception in intact adult mice for 7 days and then on mechanical allodynia in mice over 7 days in a spared nerve injury (SNI) model of neuropathic pain.

EXAMPLES

A. Method of manufacture of 11β-hydroxy-4-androstene-3,17-dione

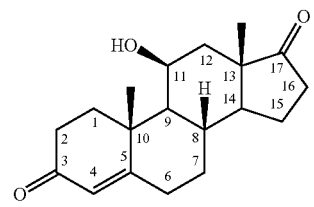

11β-Hydroxy-4-androstene-3,17-dione was synthesised in a single stage, oxidative reaction from hydrocortisone. The starting material was dissolved in acetic acid and allowed to react with sodium bismuthate overnight in the dark. The mixture was then filtered and washed with dichloromethane. The organic phase was separated, washed with water and neutralised with sodium bicarbonate (to pH 8). The organic phase was again separated and then washed, dried and filtered. Finally, the organic solvent was removed under reduced pressure. Pure product was achieved by recrystallising from ethyl acetate/heptane.

B. Biological Methods

Animals

All animals were fed standard chow and water ad libitum. Animal care and procedures were performed within the United Kingdom Home Office protocols and guidelines. Age (10-12 weeks, 25-30 g) matched adult mice were used in all experiments (n=8/genotype).

Surgery

Mice were anaesthetised with Hypnorm (Fentanyl citrate 0.315 mg/ml+Fluanisone 10 mg/ml, Jansson):Hypnovel (Midazolam 5 mg/ml, Roche):water at a ratio of 1:1:2 at 4 μl/g. The recently described SNI model of neuropathic pain was used (Holmes et al (2003) Proc. Natl. Acad. Sci. U.S.A. 100 6180-6185). The spared nerve injury model (SNI), is performed by ligation of two branches of the sciatic nerve after it trifurcates, leaving one branch intact. This procedure generates a partial denervation of the sciatic nerve which induces allodynia and an expansion of the receptive pain field. The pain behaviours in these models closely resemble a number of human neuropathic pain conditions, such as those associated with diabetes mellitus, alcoholism and trauma [Decosterd and Woolf (2000) Pain 87 149-158; Woolf and Doubell (1994) Curr. Opin. Neubiol. 4 525-534]. An incision was made in the lateral right hind leg just above the level of the knee, exposing the three terminal branches of the sciatic nerve: the common peroneal, tibial and sural nerves. The common peroneal and sural nerves were tightly ligated with 7/0 silk and sectioned distal to the ligation removing approximately 2 mm of distal nerve stump. The tibial branch remained untouched during the procedure. The overlying muscle and skin was sutured and the animals allowed to recover. In sham-operated animals the sciatic nerve branches were exposed but not lesioned.

Behavioural Testing

In all tests, the examiner was blind to the genotype of the mice. Mechanical thresholds were measured with a series of calibrated von Frey filaments (Stoeling) from 0.005 g to a maximum of 3.63 g. Animals were put in Perspex enclosures placed on an elevated grid (Ugo Basile) and habituated for at least 2 h prior to testing. Mechanical sensitivity was assessed on each hind paw, employing the up-down testing paradigm to determine the threshold force required to elicit a withdrawal response to 50% of stimulations [F. E. Holmes, A. Bacon, R. J. Pope, P. A. Vanderplank, N. C. Kerr, M. Sukumaran, V. Pachnis, and D. Wynick. Transgenic overexpression of galanin in the dorsal root ganglia modulates pain-related behaviour. *Proceedings of the National Academy of Sciences of the United States of America* 100 (10):6180-6185, (2003)].

Effect of 11β-hydroxy-Δ4-androstene-3,17-dione on Mechanosensory Nociception in Mice 11β-hydroxy-Δ4-androstene-3,17-dione was administered to 8 adult male mice aged 10-12 weeks of age daily at 9.00 am by oral gavage for two weeks. On day 8 an SNI lesion was performed. At 2 pm on the days when testing took place, mechanosensory thresholds were measured. The results showed that 11β-hydroxy-Δ4-androstene-3,17-dione markedly and significantly attenuated mechanosensory allodynia (chronic pain behaviour) when measured at 2 pm daily (or every other day) over a 7 day period after SNI surgery. The results are shown in FIG. 1

Surprisingly, the compounds of the present invention are inactive in a simple pain model where pain is caused by excessive mechanical stimulation. They are, however, active in the SNI model, which is a neuropathic pain model, thus indicating that these compounds are effective against neuropathic pain.

The invention claimed is:

1. A method of treating a subject for neuropathic pain comprising administering to the subject an effective amount of 11-hydroxy-Δ4-androstene-3,17-dione or 11-oxo-Δ4-androstene-3,17-dione.

2. The method according to claim 1 wherein the compound is 11β-hydroxy-Δ4-androstene-3,17-dione.

3. The method according to claim 1 wherein the pain is centrally mediated neuropathic pain.

4. The method according to claim 1 wherein the pain is chronic neuropathic pain, neuropathic allodynia, neuropathic hyperalgesic pain, or phantom limb syndrome.

5. The method according to claim 1 wherein the pain is one of post-herpetic neuralgia, trigeminal neuralgia, post-stroke pain, multiple sclerosis-associated pain, neuropathy-associated pain such as in idiopathic or post-traumatic neuropathy and mononeuritis, carpal tunnel-associated neuropathic pain, spinal cord injury-associated pain, fibromyalgia-associated neuropathic pain, lumbar and cervical pain, reflex sympathetic dystrophy, entrapment neuropathy, Lissauer tract section, limb amputation and stump pain, neuroma/tumour compression, Vitamin B12 deficiency, alcoholic neuropathy, neuropathic pain caused by the side effects of anti-AIDS therapies, and HIV-associated neuropathic pain.

6. The method according to claim 1 wherein the pain is cancer related pain due to tumor invasion of a nerve, pain caused by peripheral nerve or spinal cord transection, or pain caused by peripheral nerve or spinal cord trauma.

* * * * *